United States Patent
Morgan et al.

(10) Patent No.: US 11,235,087 B2
(45) Date of Patent: Feb. 1, 2022

(54) READY-TO-USE ESTHETIC COMPOSITIONS

(71) Applicant: Galderma Holding SA, La Tour-de-Peilz (CH)

(72) Inventors: Peter Morgan, Uppsala (SE); Lubica Macakova, Stockholm (SE)

(73) Assignee: Galderma Holding SA, La Tour-de-Peilz (CH)

( * ) Notice: Subject to any disclaimer, the term of this patent is extended or adjusted under 35 U.S.C. 154(b) by 0 days.

(21) Appl. No.: 17/081,893

(22) Filed: Oct. 27, 2020

(65) Prior Publication Data

US 2021/0121602 A1 Apr. 29, 2021

Related U.S. Application Data

(60) Provisional application No. 62/926,935, filed on Oct. 28, 2019.

(51) Int. Cl.
| | |
|---|---|
| *A61L 27/18* | (2006.01) |
| *A61K 8/20* | (2006.01) |
| *A61K 8/85* | (2006.01) |
| *A61K 8/86* | (2006.01) |
| *A61K 8/04* | (2006.01) |
| *A61K 8/73* | (2006.01) |
| *A61L 2/04* | (2006.01) |
| *A61L 2/08* | (2006.01) |

(Continued)

(52) U.S. Cl.
CPC ............ *A61L 27/18* (2013.01); *A61K 8/025* (2013.01); *A61K 8/042* (2013.01); *A61K 8/20* (2013.01); *A61K 8/731* (2013.01); *A61K 8/85* (2013.01); *A61K 8/86* (2013.01); *A61L 2/04* (2013.01); *A61L 2/08* (2013.01); *A61L 27/025* (2013.01); *A61L 27/20* (2013.01); *A61L 27/52* (2013.01); *A61L 27/54* (2013.01); *A61L 27/58* (2013.01); *A61Q 19/08* (2013.01); *C08L 1/286* (2013.01); *C08L 67/04* (2013.01); *C08L 71/00* (2013.01); *A61K 2800/412* (2013.01); *A61K 2800/87* (2013.01); *A61K 2800/91* (2013.01); *A61L 2300/402* (2013.01); *A61L 2400/06* (2013.01)

(58) Field of Classification Search
None
See application file for complete search history.

(56) References Cited

U.S. PATENT DOCUMENTS

| | | |
|---|---|---|
| 7,731,758 B2 | 6/2010 | Asius et al. |
| 8,414,657 B2 | 4/2013 | Asius et al. |

(Continued)

FOREIGN PATENT DOCUMENTS

| | | | |
|---|---|---|---|
| WO | WO-2004057008 A1 * | 7/2004 | .............. C12P 7/56 |

OTHER PUBLICATIONS

International Search Report and Written Opinion on PCT PCT/IB2020/060066 dated Jan. 12, 2021 (14 pages).

*Primary Examiner* — Kyung S Chang
(74) *Attorney, Agent, or Firm* — Foley & Lardner LLP; Sunit Talapatra

(57) ABSTRACT

Described are ready-to-use injectable compositions comprising polymeric microspheres or microparticles of non-animal origin, a hydrogel comprising water and a cellulose-derivative gelling agent, and polysorbate 80. Further described are methods of using the ready-to-use injectable compositions for reparative or plastic surgery, esthetic dermatology, facial contouring, body contouring, and gingival augmentation.

27 Claims, 10 Drawing Sheets

(51) Int. Cl.

| | |
|---|---|
| *A61K 8/02* | (2006.01) |
| *A61L 27/02* | (2006.01) |
| *A61L 27/20* | (2006.01) |
| *A61L 27/52* | (2006.01) |
| *A61L 27/54* | (2006.01) |
| *A61L 27/58* | (2006.01) |
| *A61Q 19/08* | (2006.01) |
| *C08L 1/28* | (2006.01) |
| *C08L 67/04* | (2006.01) |
| *C08L 71/00* | (2006.01) |

(56) References Cited

U.S. PATENT DOCUMENTS

| | | |
|---|---|---|
| 10,105,197 B1 | 10/2018 | Colon |
| 2003/0093157 A1 | 5/2003 | Casares et al. |
| 2007/0065481 A1* | 3/2007 | Chudzik ............... A61L 29/085 424/426 |
| 2009/0011045 A1* | 1/2009 | Merlin .................. A61P 31/10 424/618 |
| 2012/0231046 A1 | 9/2012 | Asius et al. |
| 2016/0106718 A1* | 4/2016 | Gupta ............... A61K 2300/00 514/58 |

* cited by examiner

READY-TO-USE ESTHETIC COMPOSITIONS

CROSS-REFERENCE TO RELATED APPLICATIONS

This application claims the benefit of priority to U.S. Application No. 62/926,935, filed Oct. 28, 2019, which is herein incorporated by reference in its entirety.

FIELD

The present disclosure relates to a ready to use implant for subcutaneous or intradermal injection, which may be used in humans in reparative or plastic surgery and in esthetic dermatology, as a dermal filler utilized for filling wrinkles, filling fine lines, filling skin cracks, filling scars, filling gingival tissue, sculpting various regions of the body, and facial sculpting.

BACKGROUND

Applicant markets a product by the trade name SCULPTRA that is supplied as a sterile freeze-dried powder in a glass vial, wherein each vial contains poly-L-lactic acid (PLLA), sodium carboxymethylcellulose (CMC), and mannitol. Prior to administration, the contents of the vial must be reconstituted by adding an aqueous solution or water to the vial. See U.S. Pat. Nos. 7,731,758 and 8,414,657.

The need to reconstitute the contents of the vial introduces a potential for error if contamination if the volume of liquid added to the vial is not aseptic or an inconsistency in the concentration of the final product if too much or too little volume is used to reconstitute the contents of the vial.

The aim of the present disclosure is to overcome the potential for error or inconsistency in reconstituting the contents of the vial and to further stabilize the ready-to-use product for storage prior to administration in the ready-to-use form by mitigating foaming and sedimentation of the ready-to-use product.

SUMMARY OF THE DISCLOSURE

The present disclosure is generally drawn to stable ready-to-use injectable implants and methods of performing reparative or esthetic dermatological surgery utilizing the implant.

In one aspect, the present disclosure is drawn to a composition comprising: (a) microspheres or microparticles of at least one polymer of non-animal origin selected from the group consisting of lactic acid polymers, glycolic acid polymers, and lactic acid-glycolic acid co-polymers; (b) a hydrogel comprising water and a cellulose-derivative gelling agent; and (c) polysorbate 80 in an amount between 0.05% to 1% by weight.

In some aspects, the at least one polymer is a lactic acid selected from poly-L-lactic acid, poly-D-lactic acid, and mixtures thereof. In some aspects, the at least one polymer is poly-L-lactic acid. In some aspects, the at least one polymer occurs in an amount between 5 mg/mL and 50 mg/mL.

In some aspects, the cellulose-derivative gelling agent is carboxymethylcellulose or hydroxypropylmethylcellulose. In some aspects, the cellulose-derivative gelling agent is carboxymethylcellulose. In some aspects, the carboxymethylcellulose is sodium carboxymethylcellulose. In some aspects, the cellulose-derivative gelling agent occurs in an amount between 0.5% to 4% by weight. In some aspects, the cellulose-derivative gelling agent occurs in an amount of 2% by weight. In some aspects, the polysorbate 80 occurs in an amount of 0.05% by weight.

In some aspects, the composition exhibits a viscosity less than 100 mPas. In some aspects, the composition exhibits a viscosity less than 60 mPas. In some aspects, the composition exhibits a viscosity between 5 to 45 mPas.

In some aspects, the ratio between the cellulose-derivative gelling agent and the polysorbate 80 is between 100:1 to 1:1. In some aspects, the ration between the cellulose-derivative gelling agent and the polysorbate 80 is between 50:1 and 10:1.

In some aspects, the microspheres or microparticles are bioresorbable. In some aspects, the microspheres or microparticles are bioresorbable within a period of about 1 year to about 3 years.

In some aspects, the composition comprises microspheres or microparticles at a concentration between 5 to 20 mg/mL. In some aspects, the composition comprises microspheres or microparticles at a concentration between 17 to 18 mg/mL. In some aspects, the microspheres or microparticles are between about 20 to 100 μm in size. In some aspects, the microspheres or microparticles exhibit a median size of about 40 μm in size. In some aspects, the microspheres or microparticles exhibit a molecular weight of between 70 to 500 kDa. In some aspects, the microspheres or microparticles exhibit a molecular weight of between 70 to 200 kDa.

In some aspects, the composition further comprises a local anesthetic. In some aspects, the local anesthetic is a amide-type or ester-type local anesthetic. In some aspects, the local anesthetic is selected from the group consisting of: bupivacaine, butanilicaine, carticaine, cinchocaine (dibucaine), clibucaine, ethyl parapiperidinoacetylaminobenzoate, etidocaine, lignocaine (lidocaine), mepivacaine, oxethazaine, prilocaine, ropivacaine, tolycaine, trimecaine, vadocaine, articaine, levobupivacaine, amylocaine, cocaine, propanocaine, clormecaine, cyclomethycaine, proxymetacaine, amethocaine (tetracaine), benzocaine, butacaine, butoxycaine, butyl aminobenzoate, chloroprocaine, dimethocaine (larocaine), oxybuprocaine, piperocaine, parethoxycaine, procaine (novocaine), propoxycaine, and tricaine; or a combination thereof.

In some aspects, the composition is aseptic. In some aspects, asepsis is achieved by irradiation or heat sterilization.

In some aspects, the composition further comprises sodium chloride, a phosphate buffer, and a pharmaceutically acceptable carrier. In some aspects, the composition exhibits a sodium chloride concentration of 0.9% w/v.

In some aspects, the composition is injectable. In some aspects, the injectable composition is an injectable implant. In another aspect, the disclosure is drawn to a pre-filled syringe or vial comprising the composition of any one of the described aspects.

In another aspect, the disclosure is drawn to an injectable implant comprising the composition of any one of the described aspects. In some aspects, the injectable implant is for intradermal or subcutaneous injection into a body of a subject in need thereof.

In another aspect, the present disclosure provides methods for performing reparative or esthetic dermatologic treatment, the method comprising injecting a subject with a composition of any one of the described aspects.

In some aspects, the injection is intradermal, subdermal, subcutaneous, intramuscular, submuscular, or intragingival. In some aspects, the injection is in one or more tissues of the oral cavity.

In some aspects, the injection is for dermal filling, body contouring, facial contouring, and gingival filling. In some aspects, dermal filling is selected from filling wrinkles, filling fine lines, filling skin cracks, filling scars, and combinations thereof. In some aspects, gingival filling comprises filling gaps between the base of teeth. In some aspects, facial and body contouring is selected from creating pronouncements of structural features; correction of concave deformities; correction of age-related facial folds; and augmenting or repairing hard or soft tissue contour defects of the face and body due to aging, injury, and acquired or congenital deformities of the face or body.

The following detailed description is exemplary and explanatory, and is intended to provide further explanation of the invention.

DETAILED DESCRIPTION OF THE DISCLOSURE

Figure 1:
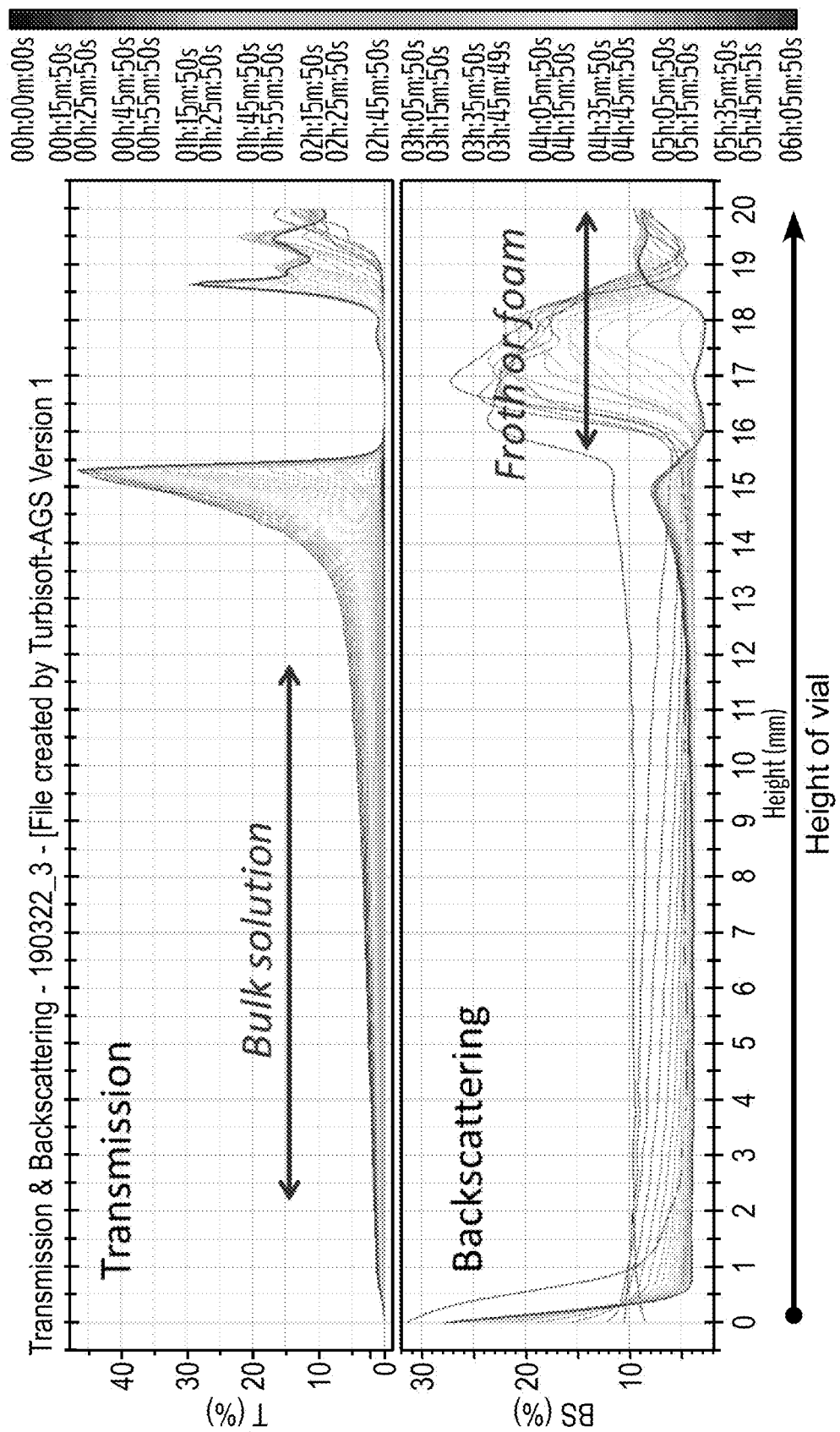
FIG. 1 depicts raw Turbiscan data (for Sample PLLA-2.25% CMC-0.05% PS80-S2). Transmission (upper part) and backscattering (lower part) by sample solutions at different heights of the vial with the sample (x-axis).

The compositions disclosed herein are ready-to-use injectable compositions comprising polymeric microspheres or microparticles of non-animal origin, a hydrogel comprising water and a cellulose-derivative gelling agent, and polysorbate 80. The methods disclosed herein are methods of using the ready-to-use injectable compositions for reparative or plastic surgery, esthetic dermatology, facial contouring, body contouring, and gingival augmentation.

The compositions and methods of use are considerable improvements over the state of the prior art given that the ready-to-use injectable compositions mitigate the potential for error or inconsistency in reconstituting a freeze-dried or lyophilized composition. The ready-to-use compositions and methods of use thereof are further improvements over the prior art considering the stability of the compositions and their superior properties that mitigate foaming and sedimentation of the ready-to-use product.

The aim of the present disclosure is to overcome the potential for error or inconsistency in reconstituting the contents of the vial and to further stabilize the ready-to-use product for storage prior to administration in the ready-to-use form by mitigating foaming and sedimentation of the ready-to-use product. Thus, the compositions and methods described herein provide a considerable achievement over the prior art.

I. Definitions

While the following terms are believed to be well understood by one of ordinary skill in the art, the following definitions are set forth to facilitate explanation of the presently disclosed subject matter.

The term "a" or "an" may refer to one or more of that entity, i.e. can refer to plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

Reference throughout this specification to "one embodiment", "an embodiment", "one aspect", or "an aspect" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics can be combined in any suitable manner in one or more embodiments.

As used herein, the terms "about" or "approximately" when preceding a numerical value indicates the value plus or minus a range of 10% of the value.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

As used herein, a "control" is an alternative sample used in an experiment for comparison purpose. A control can be "positive" or "negative." A "control sample" or "reference sample" as used herein, refers to a sample or reference that acts as a control for comparison to an experimental sample. For example, an experimental sample comprises compound A, B, and C in a vial, and the control may be the same type of sample treated identically to the experimental sample, but lacking one or more of compounds A, B, or C.

As used herein, the term "effective amount" refers to a quantity sufficient to achieve a desired therapeutic and/or prophylactic effect, e.g., an amount which results in the prevention of one or more outcomes, or an increase in one more outcomes.

As used herein, the terms "individual", "patient", or "subject" can be an individual organism, a vertebrate, a mammal, or a human. In a preferred aspect, the individual, patient, or subject is a human.

As used herein, the phrase "soft tissue" refers to tissues that connect, support, or surround other structures and organs of the body. Soft tissue includes muscles, fibrous tissues, and fat.

As used herein, the phrase "soft tissue augmentation" refers to any type of volume augmentation of soft tissues, including, but not limited to facial contouring (e.g., more pronounced cheeks, chin, or lips), correction of concave deformities (e.g., post-traumatic or HIV-associated lipoatrophy), and correction of deep age-related facial folds. Thus, soft tissue augmentation may be used for cosmetic purposes or for medical purposes, such as those following trauma or degenerative disease. Soft tissue augmentation further refers to dermal filling, body contouring, and gingival filling.

As used herein, the terms "microparticles" and "microspheres" are used somewhat interchangeably, the only distinction being that microspheres are spherical and microparticles are aspherical.

As used herein, the phrase "non-animal origin" refers to a source that excludes animals, but includes sources such as yeast, bacteria, or synthetic.

As used herein, the term "bioresorbable" refers to a degradation event or events—bioresorbable substances may dissolve, may be phagocytized, or may simply degrade over a period of time such that the substances are cleared from the body, organ, tissue, location, or cell over a period of time. The substances or degradation products thereof may be metabolized, incorporated into other molecules or compounds, or excreted.

As used herein, the term "aseptic" refers to something that is free or freed from pathogenic microorganisms.

As used herein, the term "sterile" refers to something that is free of living organisms, generally free of living microorganisms.

As used herein, the term "injectable" refers to the ability to inject a composition of the present disclosure through a 21 G, 22 G, 23 G, 24 G, 25 G, 26 G, 27 G, or 30 G needle.

The present technology is not to be limited in terms of the particular aspects described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

As used herein, the phrase "ready-to-use composition" refers to a composition of the present disclosure that does not require reconstituting the composition or further adding one or more components prior to use. A ready-to-use composition of the present disclosure is ready to be injected into a subject once the ready-to-use composition is drawn into or placed into a device used for injections, such as a syringe and needle.

As used herein, "SCULPTRA", a trade name, refers to a lyophilized or dehydrated product comprising 150 mg poly-L-lactic acid (PLLA), 90 mg of carboxymethylcellulose (CMC), and 127.5 mg of mannitol; all of which is combined in a sealed container/vial.

II. Fillers

Fillers such as dermal fillers have been used to repair, restore or augment hard or soft tissue contour defects of the body due to aging, injury, or acquired or congenital deformities of the face, body and internal organs. Fillers may be natural or synthetic substances that are used to reduce wrinkles and/or fine lines, restore lost volume, hydrate the skin, soften nasolabial folds, augment and contour lips, improve scars (depressed, hypertrophic and keloid scars), strengthen weakened vocal cords, and provide other soft tissue improvements. Substances that have been utilized include fat, paraffin, human collagen, bovine collagen, silicone, hyaluronic acids, lactic acids, and glycolic acids. In 1981, a new era in soft tissue fillers emerged with the FDA approval of bovine collagen. Since then, many soft tissue fillers have emerged. The dramatic increase in the number of current and investigational fillers has been fueled by many factors including improvements in biotechnology and an emphasis on cosmetic appearance in society. With the introduction of newer fillers, there has been an ongoing need to evaluate their risk/benefit profiles and define their limitations in order to maximize patient cosmetic outcomes and safety.

In some aspects, compositions of the present disclosure include (a) microspheres or microparticles of at least one polymer of non-animal origin selected from the group consisting of lactic acid polymers, glycolic acid polymers, and lactic acid-glycolic acid co-polymers; (b) a hydrogel comprising water and a cellulose-derivative gelling agent; and (c) a surfactant.

In some aspects, the surfactant can be selected from one or more of the group consisting of polyoxyethylene (20) sorbitan monolaurate (PS20), polyoxyethylene (20) sorbitan monopalmitate (PS40), polyoxyethylene (20) sorbitan monostearate (PS60), polyoxyethylene (20) sorbitan, PEG-20 stearate, PEG-32 stearate, caprylo caproyl polyoxyl-8 glycerides, lauroyl macrogol-32 glycerides, stearoyl macrogol-32 glycerides, polyglycerol and fatty acid esters such as polyglyceryl-3 oleate, polyglyceryl-6 dioleate, polyglyceryl-6 isostearate. poloxamer 188, poloxamer 407, sodium docusate, PEG-40 castor oil, and polysorbate 80 (PS80). In some aspects, the surfactant is polysorbate 80.

In some aspects, the surfactant is present in an amount between about 0.05% and about 1% by weight. In some aspects, the surfactant is present in an amount between 0.05% and 1% by weight.

In some aspects, the surfactant is present at about 0.05%, about 0.06%, about 0.07%, about 0.08%, about 0.09%, about 0.10%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, or about 1% by weight. In some aspects, the surfactant is present at 0.05%, 0.06%, 0.07%, 0.08%, 0.09%, 0.10%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, or 1% by weight.

In some aspects, the at least one polymer of the microspheres or microparticles is selected from synthetic aliphatic polyester particles, such as polylactic acid, polycaprolactone, glycolic acid, polyglycolic acid or co-polymers thereof. In some aspects, the at least one polymer is a poly-L-lactic acid, a poly-D-lactic acid, or a mixture thereof. In some aspects, the at least one polymer is a poly-L-lactic acid.

In some aspects, the at least one polymer occurs in an amount between 5 mg/mL to 50 mg/mL. In some aspects, the at least one polymer occurs in an amount between about 5 mg/mL to about 50 mg/mL. In some aspects, the at least one polymer occurs in an amount between 5 mg/mL to 20 mg/mL. In some aspects, the at least one polymer occurs in an amount between about 5 mg/mL to about 20 mg/mL. In some aspects, the at least one polymer occurs in an amount between 5 mg/mL to 10 mg/mL. In some aspects, the at least one polymer occurs in an amount between about 5 mg/mL to about 10 mg/mL. In some aspects, the at least one polymer occurs in an amount between 10 mg/mL to 20 mg/mL. In some aspects, the at least one polymer occurs in an amount between about 10 mg/mL to about 20 mg/mL. In some aspects, the at least one polymer occurs in an amount between 15 mg/mL to 20 mg/mL. In some aspects, the at least one polymer occurs in an amount between about 15 mg/mL to about 20 mg/mL. In some aspects, the at least one polymer occurs in an amount between 17 mg/mL to 18 mg/mL. In some aspects, the at least one polymer occurs in an amount between about 17 mg/mL to about 18 mg/mL.

In some aspects, the at least one polymer is present at about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL, about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL, about 42 mg/mL, about 43 mg/mL, about 44 mg/mL, about 45 mg/mL, about 46 mg/mL, about 47 mg/mL, about 48 mg/mL, about 49 mg/mL, or about 50 mg/mL.

In some aspects, the at least one polymer is present at 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, 30 mg/mL, 31 mg/mL, 32 mg/mL, 33 mg/mL, 34 mg/mL, 35 mg/mL, 36 mg/mL, 37 mg/mL, 38 mg/mL, 39 mg/mL, 40 mg/mL, 41 mg/mL, 42 mg/mL, 43 mg/mL, 44 mg/mL, 45 mg/mL, 46 mg/mL, 47 mg/mL, 48 mg/mL, 49 mg/mL, or 50 mg/mL.

In some aspects, the concentrations of the at least one polymer are the same as the concentrations of the microspheres or microparticles because they comprise the at least one polymer.

In some aspects, the cellulose-derivative gelling agent is selected from the group consisting of carboxymethylcellulose, methylcellulose, ethylcellulose, hydroxyethylcellulose, hydroxypropylcellulose, hydroxypropylcellulose, hydroxypropylmethylcellulose, and ethylhydroxyethylcellulose. In some aspects, the composition comprises at least one cellulose-derivative gelling agent. In some aspects, the composition comprises two cellulose-derivative gelling agents. In some aspects, the cellulose-derivative gelling agent is carboxymethylcellulose. In some aspects, the cellulose-derivative gelling agent is sodium carboxymethylcellulose. In some aspects, more than one.

In some aspects, the cellulose-derivative gelling agent occurs in an amount between 0.5% to 4% by weight. In some aspects, the cellulose-derivative gelling agent occurs in an amount between about 0.5% to about 4% by weight. In some aspects, the cellulose-derivative gelling agent occurs in an amount between 1% to 3% by weight. In some aspects, the cellulose-derivative gelling agent occurs in an amount between about 1% to about 3% by weight. In some aspects, the cellulose-derivative gelling agent occurs in an amount between 1% to 2% by weight. In some aspects, the cellulose-derivative gelling agent occurs in an amount between about 1% to about 2% by weight. In some aspects, the cellulose-derivative gelling agent occurs in an amount between 2% to 3% by weight. In some aspects, the cellulose-derivative gelling agent occurs in an amount between about 2% to about 3% by weight.

In some aspects, the cellulose-derivative gelling agent is present at 0.5%, 0.6%, 0.7%, 0.8%, 0.9%, 1%, 1.25%, 1.5%, 1.75%, 2%, 2.25%, 2.5%, 2.75%, 3%, 3.25%, 3.5%, 3.75%, or 4% by weight.

In some aspects, the cellulose-derivative gelling agent is present at about 0.5%, about 0.6%, about 0.7%, about 0.8%, about 0.9%, about 1%, about 1.25%, about 1.5%, about 1.75%, about 2%, about 2.25%, about 2.5%, about 2.75%, about 3%, about 3.25%, about 3.5%, about 3.75%, or about 4% by weight.

In some aspects, the cellulose-derivative gelling agent is present in the composition at a concentration of between 90 mg/mL to 200 mg/mL. In some aspects, the cellulose-derivative gelling agent is present in the composition at a concentration of between about 90 mg/mL to about 200 mg/mL. In some aspects, the cellulose-derivative gelling agent is present in the composition at a concentration of between 120 mg/mL to 200 mg/mL. In some aspects, the cellulose-derivative gelling agent is present in the composition at a concentration of between about 120 mg/mL to about 200 mg/mL. In some aspects, the cellulose-derivative gelling agent is present in the composition at a concentration of between 150 mg/mL to 200 mg/mL. In some aspects, the cellulose-derivative gelling agent is present in the composition at a concentration of between about 150 mg/mL to about 200 mg/mL. In some aspects, the cellulose-derivative gelling agent is present in the composition at a concentration of between 160 mg/mL to 190 mg/mL. In some aspects, the cellulose-derivative gelling agent is present in the composition at a concentration of between about 160 mg/mL to about 190 mg/mL. In some aspects, the cellulose-derivative gelling agent is present in the composition at a concentration of between 170 mg/mL to 180 mg/mL. In some aspects, the cellulose-derivative gelling agent is present in the composition at a concentration of between about 170 mg/mL to about 180 mg/mL.

In some aspects, the ratio between the cellulose-derivative gelling agent and the surfactant is between 100:1 to 1:1. In some aspects, the ratio between the cellulose-derivative gelling agent and the surfactant is between about 100:1 to about 1:1.

In some aspects, the ratio between the cellulose-derivative gelling agent and the surfactant is between 50:1 to 1:1. In some aspects, the ration between the cellulose-derivative gelling agent and the surfactant is between 50:1 to 10:1. In some aspects, the ratio between the cellulose-derivative gelling agent and the surfactant is between about 50:1 to about 1:1. In some aspects, the ratio between the cellulose-derivative gelling agent and the surfactant is between 20:1 to 1:1. In some aspects, the ratio between the cellulose-derivative gelling agent and the surfactant is between about 20:1 to about 1:1. In some aspects, the ratio between the cellulose-derivative gelling agent and the surfactant is between 10:1 to 1:1. In some aspects, the ratio between the cellulose-derivative gelling agent and the surfactant is between about 10:1 to about 1:1. In some aspects, the ratio between the cellulose-derivative gelling agent and the surfactant is between 5:1 to 1:1. In some aspects, the ratio between the cellulose-derivative gelling agent and the surfactant is between about 5:1 to about 1:1.

In some aspects, the cellulose-derivative decreases, mitigates, or slows down the sedimentation of the microparticles or microspheres in the composition, as compared to composition lacking the cellulose-derivative. In some aspects, the cellulose-derivative at a concentration of about 2% to about 3% by weight decreases, mitigates, or slows down the sedimentation of the microparticles or microspheres in the composition, as compared to a composition lacking the cellulose-derivative or having the cellulose-derivative outside of the concentration of about 2% to about 3% by weight. However, this does not decrease or mitigate foaming of the microparticles or microspheres.

In some aspects, the cellulose-derivative decreases, mitigates, or slows down the rate of sedimentation of the microparticles or microspheres, after shaking (resuspension), in the ready-to-use composition by at least about 5%, at least about 10%, at least about 20%, at least about 30%, at least about 40%, at least about 50%, at least about 60%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%, as compared to a control composition either lacking the cellulose derivative or containing an amount outside of a concentration of about 2% to about 3% by weight.

In some aspects, the compositions, after shaking (resuspension), exhibit less than 20%, less than 15%, less than 5%, less than 4%, less than 3%, less than 2%, less than 1%, and preferably substantially no sedimentation when observed at 20-22° C. after 2 hours. In some aspects, the compositions exhibit less than 20%, less than 15%, less than 5%, less than 4%, less than 3%, less than 2%, less than 1%, and preferably substantially no sedimentation when observed at 20-22° C. after about 2, about 6, about 12, about 24, or about 36 hours. In some aspects, the compositions exhibit less than 20%, less than 15%, less than 5%, less than 4%, less than 3%, less than 2%, less than 1%, and preferably substantially no sedimentation when observed at 20-22° C. after about 2-36 hours, about 2-24 hours, about 2-12 hours, about 2-6 hours, about 2-4 hours, about 12-36 hours, about 12-24 hours, or about 24-36 hours.

In some aspects, the surfactant acts as a stabilizer in the composition. In some aspects, the surfactant decreases the amount of foaming of the composition due to aggregation of the microparticles or microspheres, as compared to a composition lacking the surfactant. In some aspects, foaming of the composition does not occur or is decreased due to the presence of a surfactant, preferably polysorbate 80, at a concentration between 0.05 to 0.1% by weight, as compared to a composition lacking the surfactant or having a surfactant at a concentration outside of the range of between 0.05 to 1% by weight or 0.05 to 0.1% by weight.

In some aspects, the surfactant decreases or mitigates the amount of foaming in the ready-to-use composition, after shaking, by at least about 5%, at least about 10%, at least about 20%, at least about 30%, at least about 40%, at least about 50%, at least about 60%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%, as compared to a control composition either lacking the surfactant, preferably polysorbate 80, or containing an amount outside of a concentration of between about 0.05% to about 1% by weight.

In some aspects, the compositions exhibit less than 20%, less than 15%, less than 5%, less than 4%, less than 3%, less than 2%, less than 1%, and preferably substantially no foaming after shaking when observed at 20-22° C. after 1 day. In some aspects, the compositions exhibit less than 20%, less than 15%, less than 5%, less than 4%, less than 3%, less than 2%, less than 1%, and preferably substantially no foaming after shaking when observed at 20-22° C. after about 0.5, about 1, about 1.5, about 2, about 2.5, about 3, about 3.5, about 4, about 4.5, about 5, about 5.5, about 6, about 6.5, about 7, about 10, about 12, about 24, or about 36 hours. In some aspects, the compositions exhibit less than 20%, less than 15%, less than 5%, less than 4%, less than 3%, less than 2%, less than 1%, and preferably substantially no foaming after shaking when observed at 20-22° C. after about 0.5-36 hours, about 0.5-12 hours, about 0.5-6 hours, about 0.5-3 hours, about 0.5-2 hours, about 0.5-1.5 hours, about 0.5-1 hour, about 1-1.5 hours, about 1-2 hours, about 1-4 hours, about 1-6 hours, about 2-3 hours, about 2-4 hours, or about 2-6 hours.

In some aspects the composition is bioresorbable. In some aspects, the microspheres or microparticles are bioresorbable. In some aspects, the composition is bioresorbed within a period of about 1 year to about 3 years. In some aspects, the composition is bioresorbed within a period of 1 year to 3 years. In some aspects, the microspheres or microparticles are bioresorbed within a period of about 1 year to about 3 years. In some aspects, the microspheres or microparticles are bioresorbed within a period of 1 year to 3 years.

In some aspects, the composition comprises one or more thickeners selected from dextrin, hydroxyethylstarch, microcrystalline cellulose, carboxymethylated starch, acylated starch, xanthan gum, gellan gum, hyaluronic acid, carrageenan, pectin, and sodium alginate.

In some aspects, the composition exhibits a viscosity less than 100 mPas. In some aspects, the composition exhibits a viscosity less than about 100 mPas. In some aspects, the composition exhibits a viscosity less than 60 mPas. In some aspects, the composition exhibits a viscosity less than about 60 mPas.

In some aspects, the composition exhibits a viscosity between 5 to 45 mPas. In some aspects, the composition exhibits a viscosity between about 5 to about 45 mPas.

In some aspects, the composition exhibits a viscosity between 5 to 45 mPas, between 10 to 45 mPas, between 20 to 45 mPas, between 30 to 45 mPas, between 5 to 30 mPas, or between 5 to 20 mPas, between 5 to 10 mPas. In some aspects, the composition exhibits a viscosity between about 5 to about 45 mPas, between about 10 to about 45 mPas, between about 20 to about 45 mPas, between about 30 to about 45 mPas, between about 5 to about 30 mPas, or between about 5 to about 20 mPas, between about 5 to about 10 mPas.

In some aspects, the composition exhibits a viscosity less than 95 mPas, less than 90 mPas, less than 85 mPas, less than 80 mPas, less than 75 mPas, less than 70 mPas, less than 65 mPas, less than 60 mPas, less than 55 mPas, less than 50 mPas, less than 45 mPas, less than 40 mPas, less than 35 mPas, less than 30 mPas, less than 25 mPas, less than 20 mPas, less than 15 mPas, less than 10 mPas, or less than 5 mPas. In some aspects, the composition exhibits a viscosity less than about 95 mPas, less than about 90 mPas, less than about 85 mPas, less than about 80 mPas, less than about 75 mPas, less than about 70 mPas, less than about 65 mPas, less than about 60 mPas, less than about 55 mPas, less than about 50 mPas, less than about 45 mPas, less than about 40 mPas, less than about 35 mPas, less than about 30 mPas, less than about 25 mPas, less than about 20 mPas, less than about 15 mPas, less than about 10 mPas, or less than about 5 mPas.

In some aspects, the microspheres or microparticles are between 20 to 100 μm in size. In some aspects, the microspheres or microparticles are between about 20 to about 100 μm in size. In some aspect, this size may be length, diameter, or width. In general, this refers to diameter.

In some aspects, the microspheres or microparticles are between 20 to 100 μm, between 20 to 80 μm, between 20 to 60 μm, between 20 to 40 μm, between 30 to 100 μm, between 40 to 100 μm, between 50 to 100 μm, between 60 to 100 μm, between 70 to 100 μm, or between 80 to 100 μm in size. In some aspects, the microspheres or microparticles are between about 20 to about 100 μm, between about 20 to about 80 μm, between about 20 to about 60 μm, between about 20 to about 40 μm, between about 30 to about 100 μm, between about 40 to about 100 μm, between about 50 to about 100 μm, between about 60 to about 100 μm, between about 70 to about 100 μm, or between about 80 to about 100 μm in size.

In some aspects, the microspheres or microparticles exhibit a molecular weight of between 50 to 500 kDa. In some aspects, the microspheres or microparticles exhibit a molecular weight of between about 50 to about 500 kDa. In some aspects, the microspheres or microparticles exhibit a molecular weight of between 50 to 200 kDa. In some aspects, the microspheres or microparticles exhibit a molecular weight of between about 70 to about 200 kDa. In some aspects, the microspheres or microparticles exhibit a molecular weight of between 50 to 140 kDa. In some aspects, the microspheres or microparticles exhibit a molecular weight of between about 50 to about 140 kDa.

In some aspects, the composition further comprises a local anesthetic. In some aspects, the composition comprises at least one local anesthetic. In some aspects the local anesthetic is an amide-type local anesthetic. In some aspects, the local anesthetic is an ester-type local anesthetic.

In some aspects, the local anesthetic is selected from the group consisting of: bupivacaine, butanilicaine, carticaine, cinchocaine (dibucaine), clibucaine, ethyl parapiperidinoacetylaminobenzoate, etidocaine, lignocaine (lidocaine), mepivacaine, oxethazaine, prilocaine, ropivacaine, tolycaine, trimecaine, vadocaine, articaine, levobupivacaine, amylocaine, cocaine, propanocaine, clormecaine, cyclomethycaine, proxymetacaine, amethocaine (tetracaine), benzocaine, butacaine, butoxycaine, butyl aminobenzoate, chloroprocaine, dimethocaine (larocaine), oxybuprocaine, piperocaine, parethoxycaine, procaine (novocaine), propoxycaine, and tricaine; or a combination thereof.

In some aspects, the concentration of local anesthetic in the composition is between 1 to 5 mg/mL. In some aspects, the concentration of local anesthetic in the composition is between about 1 to about 5 mg/mL. In some aspects, the concentration of local anesthetic in the composition is between 2 to 4 mg/mL. In some aspects, the concentration of local anesthetic in the composition is between about 2 to about 4 mg/mL. In some aspects, the concentration of local anesthetic in the composition is 0.5 mg/mL, 1 mg/mL, 1.5 mg/mL, 2 mg/mL, 2.5 mg/mL, 3 mg/mL, 3.5 mg/mL, 4 mg/mL, 4.5 mg/mL, or 5 mg/mL. In some aspects, the concentration of local anesthetic in the composition is about 0.5 mg/mL, about 1 mg/mL, about 1.5 mg/mL, about 2 mg/mL, about 2.5 mg/mL, about 3 mg/mL, about 3.5 mg/mL, about 4 mg/mL, about 4.5 mg/mL, or about 5 mg/mL.

In some aspects, the composition is injectable. In some aspects, the injectable composition is an injectable implant. In some aspects, the disclosure is drawn to an injectable implant comprising any one of the compositions disclosed herein. In some aspects, the injectable implant is for subdermal, intradermal, subcutaneous, intramuscular, submuscular, intragingival injection.

In some aspects, the disclosure is drawn to a pre-filled syringe comprising any one of the compositions disclosed herein. In some aspects, the disclosure is drawn to a pre-filled vial comprising any one of the compositions disclosed herein.

In some aspects, a kit comprises a pre-filled syringe comprising any one of the compositions disclosed herein. In some aspects, a kit comprises a pre-filled vial comprising any one of the compositions disclosed herein, a syringe, and one or more hypodermic needles. In some cases the kit comprises an antimicrobial composition for administering to the site of injection.

In some aspects, kits for use in practicing the methods described herein are contemplated. In some aspects, kits comprise all solutions, buffers, compounds, vessels, and/or instructions sufficient for performing the methods described herein.

In some aspects, the composition further comprises sodium chloride. In some aspects, the composition exhibits a sodium chloride concentration of 0.9% w/v. In some aspects, the composition further comprises a phosphate buffer. In some aspects, the composition further comprises a pharmaceutically acceptable carrier. In some aspects the composition further comprises sodium chloride, a phosphate buffer, and a pharmaceutically acceptable carrier.

In some aspects, the composition comprises one or more density enhancing agents. In some aspects, the density enhancing agents may be selected from sorbitol, mannitol, and fructose.

In some aspects, the composition comprises a buffering agent. A buffering agent is a chemical compound that is or compounds that are added to a solution to allow that solution to resist changes in pH as a result of either dilution or small additions of acids or bases. Effective buffer systems employ solutions which contain large and approximately equal concentrations of a conjugate acid-base pair (or buffering agents). A buffering agent employed herein may be any such chemical compound(s) which is pharmaceutically acceptable, including but not limited to salts (conjugates acids and/or bases) of phosphates and citrates. In some aspects, the buffering agent comprises phosphate buffered saline (PBS) or an alternative phosphate buffer.

In some aspects, the composition has a pH between 5.5 to 7.5. In some aspects, the composition has a pH between about 5.5 and about 7.5. In some aspects, the composition has a pH between 6.5 to 7.5. In some aspects, the composition has a pH between about 6.5 and about 7.5. In some aspects, the composition has a pH between 5.5 to 6.5. In some aspects, the composition has a pH between about 5.5 and about 6.5. In some aspects, the composition has a pH between 5 to 7. In some aspects, the composition has a pH between about 5 and about 7. In some aspects, the composition has a pH between 6 to 7. In some aspects, the composition has a pH between about 6 and about 7.

In some aspects, the composition has a pH of 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In some aspects, the composition has a pH of about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

In some aspects, the composition is aseptic. In some aspects, the composition is sterile. In some aspects, the composition is sterilized via filtration sterilization, heat sterilization, or irradiation sterilization. In some aspects, components of the composition are sterilized prior to mixing or forming the whole composition, thus resulting in a composition that comprises two or more components that were sterilized prior to forming the composition.

In some aspects, the poly-L-lactic acid (PLLA) is an active compound that stimulates collagen production.

In some aspects, the ready-to-use composition comprises 150 mg of PLLA microparticles or microspheres (non-irradiated), 10 mM phosphate buffer (pH 6.2), isotonic sodium chloride, 0.5% polysorbate 80, 180 mg CMC, and 8 mL of water.

In some aspects, the ready-to-use composition comprises 150 mg of PLLA microparticles or microspheres (irradiated), lidocaine hcl (3 mg/mL), 10 mM phosphate buffer (pH 6.2), isotonic sodium chloride, 0.5% polysorbate 80, 180 mg CMC, and 8 mL of water.

Preparing Formulation 1: Sterile Formulation with No Lidocaine

Background Buffer 1
10 mM phosphate buffer with added sodium chloride prepared and adjusted to pH 6.2
Corresponding amount of carboxymethylcellulose (22.5 mg/ml) slowly added into the buffer while stirring and left overnight under stirring conditions until completely dissolved
Corresponding amount of PS80 was added (0.05%) and mixed for about 20 minutes
Resulting solution was autoclaved at 125° C. for 8 minutes Mixing of Samples to Produce Final Ready-to-Use Formulation 1
150 mg of sterilized PLLA is added to a vial
8 mL of background buffer 1 is added to the vial containing the PLLA
Samples are vigorously vortexed for 1 minute until PLLA is properly dispersed Preparing Formulation 2: Sterile Formulation with Lidocaine (Terminally Sterilized)

Background Buffer 2
10 mM phosphate buffer with added sodium chloride prepared and adjusted to pH 6.2
Corresponding amount of carboxymethylcellulose (22.5 mg/mL) was slowly added into the buffer while stirring and left overnight under stirring conditions until completely dissolved
Corresponding amount of PS80 was added (0.05%) and mixed for about 20 minutes
Corresponding amount of lidocaine hydrochloride (2.667 mg/mL) was a added and mixed for about 20 minutes
Mixing of Samples to Produce Final Ready-to-Use Formulation 1
150 mg of non-sterilized PLLA is added to a vial
9 mL of background buffer 2 is added to the vial containing the PLLA
Samples are vigorously vortexed for 1 minute until PLLA is properly dispersed
Samples are terminally sterilized by autoclaving at 125° C. for 8 minutes

III. Methods of Using the Fillers

In some aspects, the present disclosure comprises methods of performing reparative or esthetic dermatologic treatment. In some aspects, the reparative or esthetic dermatologic treatment comprises injecting a subject with a composition disclosed herein. In some aspects, the injection is a subdermal, intradermal, subcutaneous, intramuscular, submuscular, or intragingival injection.

In some aspects, methods of the present disclosure are drawn to intragingival injection to fill the gums as a result of receding gums. In some aspects, methods are drawn to injection of the composition in one or more tissues of the oral cavity.

In some aspects, the injection is for dermal filling, body contouring, facial contouring, and gingival filling.

In some aspects, the injection of a composition disclosed herein is for dermal filling. In some aspects, methods of dermal filling include injection of the composition to fill skin cracks. In some aspects, methods of dermal filling include injection of the composition to fill fine lines in the face, neck, hands, feet, knees, and elbows. In some aspects, methods of dermal filling include injection of the composition to fill fine wrinkles in the face, neck, hands, feet, knees, and elbows. In some aspects, methods of dermal filling include injection of the composition to fill fine lines in the face, neck, hands, feet, knees, and elbows.

In some aspects, methods of dermal filling include injection of the composition to fill scars. In some aspects, methods of dermal filling include injection of the composition to fill depressed scars. In some aspects, methods of dermal filling include injection of the composition to fill hypertrophic scars. In some aspects, methods of dermal filling include injection of the composition to fill keloid scars.

In some aspects, methods of dermal filling include injection of the composition to restore and/or correct for signs of facial fat loss (lipoatrophy) in people with human immunodeficiency virus (HIV).

In some aspects, methods of dermal filling include injection of the composition to the backs of hands or the top of feet.

In some aspects, methods of dermal filling include injection of the composition to strengthen weakened vocal cords.

In some aspects, methods of dermal filling include injection of the composition to restore lost volume to a portion of the body as a result of age, illness, or injury.

In some aspects, methods of facial contouring include injection of the composition to the face to modify the facial contour. In some aspects, methods of facial contouring include injection of the composition to the lips to augment the size and/or shape of the lips.

In some aspects, methods of facial contouring include injection of the composition to the face to increase facial symmetry. In some aspects, methods of facial contouring include injection of the composition to change the shape of the face to an oval shape, round shape, square shape, triangle shape, inverted triangle shape, rectangular shape, or oblong shape. In some aspects, methods of facial contouring include injection of the composition to increase the total width of the face. In some aspects, methods of facial contouring include injection of the composition to increase the total length of the face.

In some aspects, methods of facial contouring include injection of the composition to the face to increase the forehead and/or cheekbone width. In some aspects, methods of facial contouring include injection of the composition to the face to increase the length of the jawline.

In some aspects, methods of facial contouring include injection of the composition to the face to change the size and/or shape of the chin. In some aspects, methods of facial contouring include injection of the composition to the face to change the size and/or shape of the forehead. In some aspects, methods of facial contouring include injection of the composition to the face to change the size and/or shape of the cheeks. In some aspects, methods of facial contouring include injection of the composition to the face to change the size and/or shape of the brow.

In some aspects, methods of facial contouring include injection of the composition to the face to modify the appearance associated with retrognathia. In some aspects, methods of facial contouring include injection of the composition to the face to modify the appearance associated with prognathism.

In some aspects, methods of body contouring include injection of the composition to the body to modify the size and shape of various aspects of the body. In some aspects, methods of body contouring include injection of the composition to the body to modify the size and shape of aspects of the body to increase symmetry.

In some aspects, methods of body contouring include injection of the composition to the body to modify the size and shape of the breasts, buttocks, sacrum, groin, hips, abdomen, thorax, feet, legs, knees, popliteus, thighs, arms, hands, elbows, and/or antecubitis.

In some aspects, methods of body contouring include injection of the composition to the body to fill a concave deformity. In some aspects, the concave deformity is a result of age, illness, injury, or predisposition. In some aspects, methods of body contouring include injection of the composition to the body to decrease the appearance of cellulite.

EXAMPLES

Example 1

Improvement of Colloidal Properties of Therapeutic PLLA (Poly-L-Lactic Acid) Dispersions by Addition of Non-Ionic Surfactant and Hydrocolloids Example 1 provides the experimental materials and design utilized in Examples 1-4. The examples demonstrate the following: (1) the elimination of PLLA froth (foaming) by addition of non-ionic surfactants, (2) slowing down sedimentation of PLLA particles by addition of hydrocolloid (polymeric thickener), and (3) synergistic effect between surfactants of hydrocolloid in slowing down sedimentation rate.

TABLE 1

Materials

| Ingredient | Abbreviation |
| --- | --- |
| SCULPTRA, freeze-dried cake | SCULPTRA |
| Poly-L-lactic acid powder (non-sterilized) | PLLA |
| Sodium carboxymethycellulose | CMC |
| Polysorbate 80 | PS80 |
| Phosphate-buffered saline - pH 6.2 | buffer |
| Deionized water | MILLIQ |

Samples were prepared as follows: 150 mg of PLLA powder was weighted into standard Turbiscan vial. Then, desired amount of CMC powder and buffer were added and sample was set on magnetic stirring until CMC was fully dissolved. Alternatively, a buffer with pre-dissolved CMC was added. As last step, PS80 was added by pipetting a corresponding amount of 10% stock solution in buffer of MILLIQ water. Dispersions were then mixed by a high intensity vortexing lasting 1 minute.

For preparation of reconstituted SCULPTRA samples aiming at 150 mg PLLA per 8 ml of water, a 367.5 mg of homogenized freeze dried powder was used. This is based on the nominal composition of 150 mg PLLA, 90 mg of CMC and 127.5 mg of Mannitol per each package/vial with freeze dried formulation. The homogenized SCULPTRA powder was obtained by crushing and mixing the freeze dried cake from several vials of the same batch.

The colloidal properties of PLLA dispersions were studied by Turbiscan Lab equipment (from Formulaction Inc.). This equipment is collecting data along the height of the sample vials on:

Transmittance of light through a vial, which increases with decreasing turbidity of the samples as the dispersed particles sediment with time Backscattering of light from a vial, which is substantial from a non-transparent foam or froth and therefore the backscattering value can be used to follow foam and froth changes with time.

The measure of transmittance of light and backscattering of light of the compositions of the present disclosure allow for a determination of the amount of foaming and sedimentation that occurs in a composition. This determination of foaming and sedimentation can be compared between a variety of compositions. Data was collected at the predetermined regular time intervals, so that time development of the colloidal system could be followed.

The samples were prepared in Turbiscan glass vials of standardized size. The PLLA particles that has partly sedimented after initial mixing of samples were re-dispersed by shaking the vial prior to start of the Turbiscan data collection cycle. The presented transmission data were averaged for data collected between 2 mm and 12 mm of the vial height, which correspond to bulk part of the sample solution). The presented backscattering data were averaged for data between 16 mm and 20 mm of the vial height, which correspond to top part of sample dispersion with froth of foam. See FIG. 1.

Example 2

Elimination of PLLA Froth by Addition of Non-Ionic Surfactant Polysorbate 80

This example demonstrates the effect of the addition of non-ionic surfactants on the presence of the persistent PLLA froth.

Figure 2:
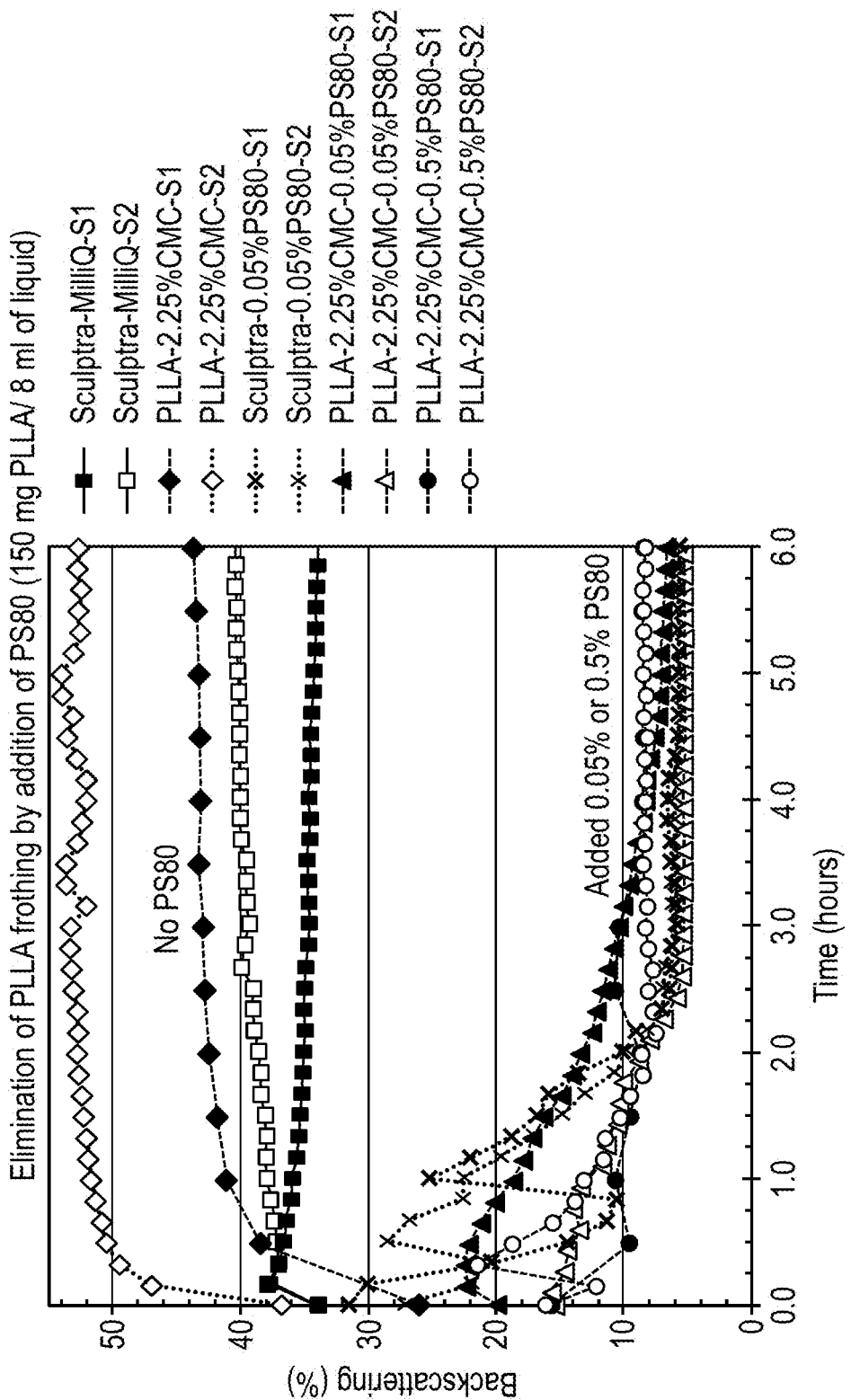
FIG. 2 depicts backscattering by froth or foam vs time in the absence and presence of non-ionic surfactant PS80 for dispersions with PLLA loading of 150 mg/8 mL.

As shown in FIG. 2, PLLA froth disappeared from PS80 concentration of 0.05%. The presence of polysorbate 80 in formulation clearly leads to elimination of the persistent PLLA froth for both formulations based off of PLLA as well as for reconstituted freeze-dried SCULPTRA formulations. Residual back-scattering in the presence of PS80 stems from an unstable surfactant based foam, which disappears (back-scattering below 10%) within about 2 hours after start of data collection cycle, when the samples are shaken to redispersed sedimented PLLA.

Since the formation of stable PLLA froth is believed to be related to the hydrophobic nature of PLLA particles and their poor wetting by water/buffer, the mechanism behind froth eliminations is very likely related to a decrease in water/buffer interfacial tension as well as the adsorption of surfactant at the surface of PLLA particles rendering their surface hydrophilic, which appeared to result in better wetting of particles by the aqueous solvent.

Based on the proposed mechanism, surfactant concentrations in the solution about critical micellar concentration or higher are required for froth elimination effect. It is important that take into account surfactant depletion from solution due to adsorption on surfaces of many small PLLA particles with large surface area, i.e. one should add more surfactants if more PLLA particles per given volume would be added.

Example 3

Slowing Down of Sedimentation of PLLA Particles by Addition of Polysaccharide Based Hydrocolloid Sodium Carboxymethylcellulose This experiment demonstrates how the addition of hydrocolloid affects sedimentation of PLLA particles in dispersions.

Results revealed that the addition of carboxymethelcellulose (CMC) significantly slows down the transmission increase rate of the samples in comparison to PLLA dispersions prepared in bare buffer. The more CMC was added, the slower was the transmission increase with time. The low transmission of light through the sample is related to its turbidity due to presence of PLLA particles floating in bulk liquid. Sedimentation rate of these particles is slower in presence of carboxymethelcellulose that increases viscosity of the solution. Since particles sediment slower, transmission is increasing less with time. The higher is the concentration of CMC, the higher is viscosity of solution and the slower is sedimentation of PLLA particles.

Considering the proposed mechanism, the target concentration of the added hydrocolloid is dependent on its properties, such as molecular weight, degree of branching, modification of side groups and other properties which affect viscosity of hydrocolloid polymer solutions. Viscosity of the 2.25% CMC in buffer solution, which resulted in similar transmission increase rate of the SCULPTRA formulation, was 28 mPas. measured by capillary viscometry. The concentration of other hydrocolloid or different type of CMC would need to be adjusted to give similar viscosity. The addition of CMC had no significant effect on PLLA froth stability. This is related to the lack of surface activity of CMC.

Example 4

Synergistic Effect Between Non-Ionic Surfactant PS80 and Polysaccharide-Based Hydrocolloid Carboxymethylcellulose This experiment demonstrates whether there is a synergistic effect between surfactants and hydrocolloid thickener in (a) slowing down the sedimentation rate, and (b) elimination of PLLA froth.

There was a synergistic effect between hydrocolloid and surfactant in slowing down sedimentation of PLLA particles. While the presence of 0.5% polysorbate 80 led to elimination of the PLLA foam even on its own (sample PLLA-buffer-0.5% PS80), the clearance rate for this formulation was still very high. On the other hand, the addition of PS80 into a formulation containing carboxymethylcellulose led to slowing down the clearance in comparison to the corresponding PS80-free formulations. The synergistic effect seems independent of the PS80 concentration, since the same low clearance rate was observed for after addition of 0.05% PS80 and 0.5% PS80. Thus, we believe that the lowering of transmittance is related to wetting of PLLA particles originally present in froth and their transfer into bulk of dispersion where they contribute to turbidity. A similar synergistic effect is expected for different PS80 concentrations as far as these are higher than PLLA particles wetting threshold.

Example 5

Buffer System for Poly-L-Lactic Acid (PLLA) Stability

PLLA is hydrolyzing in aqueous solution, which leads to the release of lactic acid monomers and oligomers from bulk polymer particles as well as to fragmentations of bulk polymers. The process is self-catalyzed by the presence of degradation products (PLLA fragments or monomers) both in solution and within bulk polymer. Sterilization and storage of PLLA in aqueous solution can lead to substantial degradation and to unacceptable alteration of the formulation properties.

The rate of PLLA degradation can be affected by properties of buffer such as buffer ionic composition (e.g., phosphate buffer, citrate, Bis-Tris); pH of the buffer; buffering capacity/concentration of buffering agents; co-solvents.

These studies evaluate the effectiveness of various buffer systems for maximizing PLLA stability or increasing the shelf-life in a ready-to-use formulation.

Development and Optimization of Analytical Methods

The unsterilized PLLA (18S0229) and gamma ray sterilized PLLA (1830200) were subject to testing.

150 mg PLLA in 5 mL MILLIQ water dispersions were prepared

Accelerated degradation was evaluated by mixing at 90° C. for two weeks

Filtered through 0.22 µm MILIPORE filters to separate water insoluble undegraded material from soluble degradation products Filtrate (water soluble portion) was analyzed by liquid chromatography after treatment with 1M NaOH in order to identify the breakdown of PLLA to lactic acid oligomers to lactic acid monomers The retentate on the filter (water insoluble) portion was dissolved in dichloromethane and analyzed by gel permeation chromatography (GPC)

Reference samples for GPC: non-degraded materials
Untreated—PLLA powders as received dissolved in CH2Cl2
Filter residue—nondegraded—filtered non-degraded PLLA dispersion dissolved in CH2CL2

Liquid chromatography was used to determine the state of standards and standards subjected to degradation. A determination of the presence of lactic acid monomers in sterilized PLLA by analysis of the filtrate was conducted—no lactic acid oligomers were detected after a one hour treatment with 1M sodium hydroxide. A type of size exclusion chromatography called gel permeation chromatography (GPC) was used to determine the sizes of PLLA.

PLLA samples were in two forms—(1) milled and unsterilized and (2) milled and gamma ray sterilized. The milled PLLA was characterized for the lactic acid content, molecular weight distribution of PLLA polymers, and the effect of autoclaving.

The low molecular weight of "Filter residue-degraded" is due to visually observed high degree of PLLA insolubility in CH2Cl2 after degradation at 90° C. for 2 weeks. The reason for that is possibly a change in the ration between amorphous PLLA/crystalline PLLA upon degradation and eventual re-crystallization above glass transition temperature. It is possible that crystalline PLLA is less soluble in CH2Cl2 and only short polymeric chains get into solution upon sample preparation step. An alternative may be that preferential degradation of amorphous part of PLLA leaving non-degraded residue highly crystalline.

The low molecular weight of "Filter residue-degraded" is due to visually observed high degree of PLLA insolubility in CH2Cl2 after degradation at 90° C. for 2 weeks, with a similar explanation as for non-sterilized sample=change in PLLA crystallinity upon high temperature degradation.

The general takeaway is that:
some part of the retentate for samples degraded at 90° C. is not solubilized in dichloromethane
for samples degraded at 90° C., possibly only the low molecular weight fraction of polymers are solubilized while the high molecular weight polymers are still left in solid phase
for the starting material PLLA powder and the non-degraded samples, there were no issues with solubility There were distinctions between the degraded unsterilized PLLA and the degraded sterilized PLLA can be seen in a single chart—the amount degraded filter residue was 37% for degraded unsterilized PLLA and 50% for degraded sterilized PLLA—corresponds to mass balance for degraded samples using 0.2 µm filters (degradation occurred for two weeks at 90° C. However, the both sets of experiments yielded a total PLLA recovery of over 100% (lactic acid monomers+filter residue), which was attributed to an experimental error. In later experiments, the filtration procedure was adjusted and a more exact follow-up on filtrate volumes was employed.

Additional experiments were carried out on unsterilized PLLA in deionized water and sterilized PLLA in deionized water—evaluating samples subjected to (1) degradation at 40° C. for 4 days, and (2) autoclaving at 125° C. for 8 minutes. The results are as follows:
There was limited degradation at 40° C. with no detectable lactic acid monomers
There was satisfactory solubility of PLLA filter residues after degradation at 40° C. for 4 days (only a very small amount was insoluble—potentially an impurity)
There was limited degradation upon autoclaving
There was satisfactory solubility of PLLA filter residues after autoclaving—only a very small amount was insoluble
There was a good reproducibility of GPC results obtained for sterilized and non-sterilized PLLA on different occasions Evaluation of PLLA Stability in Different Buffers Upon AutoClaving and Subsequent Thirty Days Storage at 40° C.

With regard to the PLLA recovery in filter residues, we assumed 150 mg of PLLA in each 367.5 mg of added freeze-dried powder. However, variation of PLLA content in SCULPTRA samples was +/−2-% and thus, less PLLA in filter residues of SCULPTRA samples is more likely a consequence of initial PLLA content variation than a consequence of PLLA degradation.

The pH 6.2 buffers, the 50 mM high buffer capacity buffer, and the lower PLLA load of 10 mg/mL samples exhibited good stability. The primary observations regarding the molecular weights of the filter residues are: (1) there was a reduction in the molecular weight for all samples in comparison to corresponding references; (2) for samples prepared in buffer with pH 6.2 and water with pH about 6 slightly smaller decrease in molecular weight than for the samples prepared in buffers with pH 7.3; and (3) there was a substantial reduction of molecular weight for the sample containing 3 mg/mL lidocaine.

In view of the substantial reduction of molecular weight for the sample containing lidocaine, the experiments were repeated, and there was a good reproducibility in the resulting data for newly mixed samples containing lidocaine.

In water, lidocaine is in equilibrium with the protonated form. At pH below the pka, the protonated from dominates, resulting in an acidic hydrolysis of lidocaine. GPC chromatography with a non-autoclaved lidocaine-containing sample compared with an autoclaved lidocaine-containing sample reveals a size shift in which the non-autoclaved lidocaine-containing sample has a GPC output that comes off at an earlier time point than the autoclaved lidocaine-containing sample. The PLLA particles are hydrophobic and their density can be significantly higher than that of water (the density is dependent of particle porosity). The colloidal stability of PLLA suspensions can be improved by the following functional ingredients.

Stabilizers—preventing aggregation driven by hydrophobic interactions between particles, e.g., by using polymers that adsorb to the PLLA particles and expose PEO groups into the bulk solution
Thickeners—preventing or slowing down sedimentation by increasing the viscosity of buffer solutions through formation of hydrogel type of structures In some aspects, an advantageous buffering system comprises the following:
10 mM phosphate buffer+NaCl, pH 6.2+3 mg/mL lidocaine Example 6

Reductions in Foaming and Sedimentation

Foaming in a ready-to-use product can be very problematic. The core SCULPTRA compositions comprise PLLA, mannitol, and CMC—and the samples have the capacity to foam.

Figure 3:
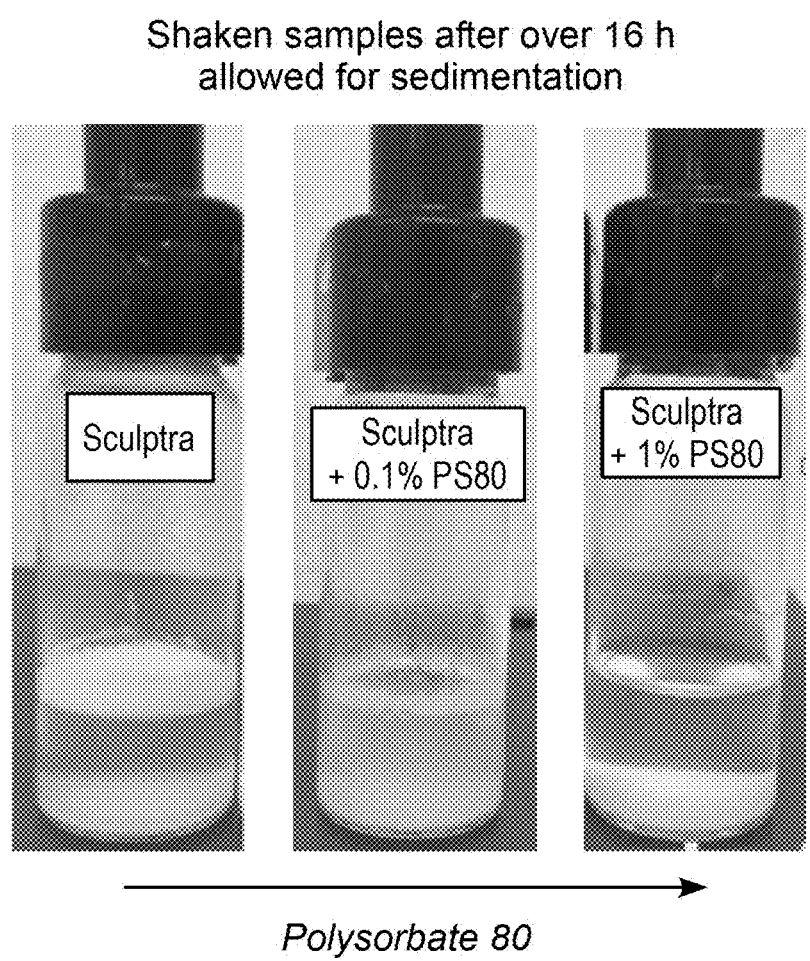
FIG. 3 depicts a comparison of three vials of SCULPTRA with the presence of absence of PS80—none on the left, 0.1% PS80 in the middle, and 1% PS80 on the right. Samples were shaken and the image was captured after 16 hours. From left to right the foaming decreases.

FIG. 3 identifies the effects of PS80 on foaming—SCULPTRA exhibits significant PLLA foaming, SCULPTRA+0.1% PS80 exhibits less PLLA foaming, and SCULPTRA+1% PS80 does not appear to exhibit any marked PLLA foaming.

TABLE 2

Sample variations and foaming.

| Label | PLLA Type | SCULPTRA | PLLA (mg) | CMC (mg) | Mannitol (mg) | Water (mL) |
|---|---|---|---|---|---|---|
| S2 | SCULPTRA | 1 pckg | 150 | 90 | 127.5 | 8 |
| P1 | Unsterilized PLLA | | 150 | | | 8 |
| P2 | Unsterilized PLLA | | 150 | 90 | | 8 |
| P3 | Unsterilized PLLA | | 150 | 90 | 127.5 | 8 |
| P4 | Unsterilized PLLA | | 150 | 180 | | 8 |

Visual identification of sample vials corresponding to the samples described in Table 2 makes it clear that PLLA foaming is not related to the freeze-drying process, the presence of mannitol, or the presence of CMC.

Figure 4:
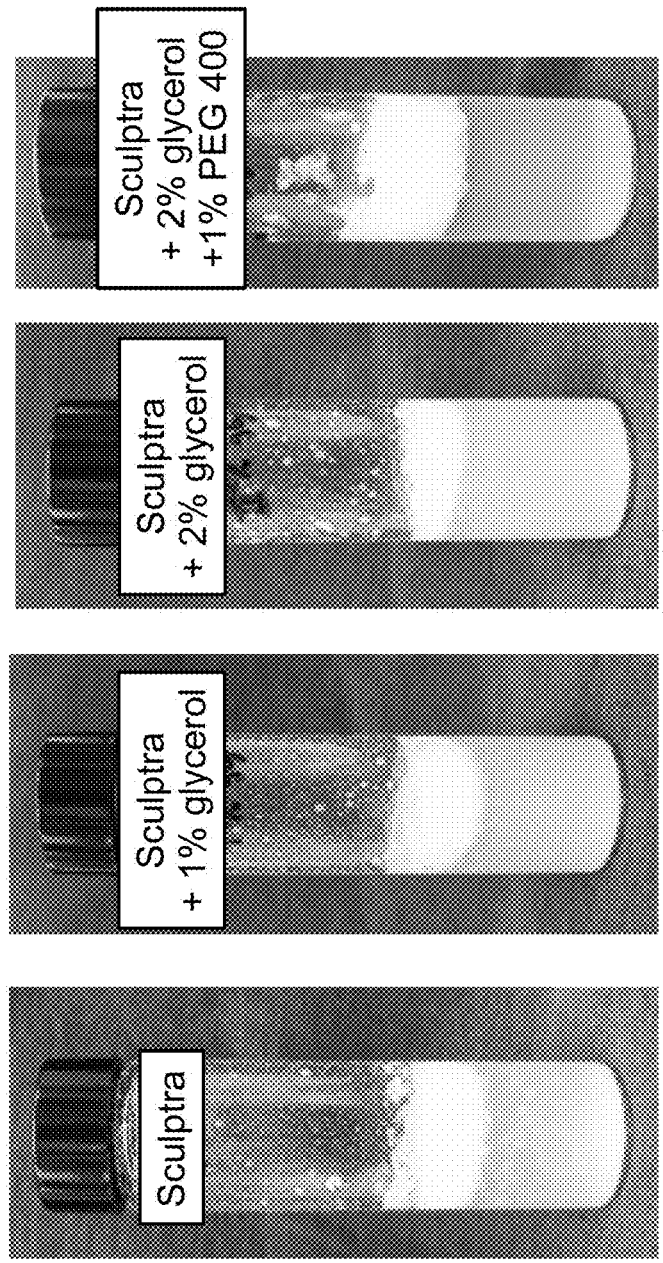
FIG. 4 depicts a comparison of four vials of SCULPTRA products—(from left to right)—SCULPTRA, SCULPTRA+1% glycerol, SCULPTRA+2% glycerol, and SCULPTRA+2% glycerol+1% PEG 400—indicating that neither glycerol nor PEG 400 mitigates PLLA foaming.

Furthermore, the size of the particles and the shape of the particles do not appear to dictate PLLA foaming. FIG. 4 suggests that neither glycerol nor PEG 400 are capable of mitigating PLLA foaming.

TABLE 3

Sample variations and sedimentation.

| Label | PLLA Type | SCULPTRA | PLLA (mg) | CMC (mg) | Mannitol (mg) | PS80 | Water (mL) |
|---|---|---|---|---|---|---|---|
| S1 | SCULPTRA | 1 pckg | 150 | 90 | 127.5 | | 8 |
| S1-0.1 | SCULPTRA | 1 pckg | 150 | 90 | 127.5 | 0.1% | 8 |
| S1-1 | SCULPTRA | 1 pckg | 150 | 90 | 127.5 | 1% | 8 |
| S2 | SCULPTRA | 1 pckg | 150 | 90 | 127.5 | | 8 |
| P1 | Unsterilized PLLA | | 150 | | | | 8 |
| P2 | Unsterilized PLLA | | 150 | 90 | | | 8 |
| P3 | Unsterilized PLLA | | 150 | 90 | 127.5 | | 8 |
| P4 | Unsterilized PLLA | | 150 | 180 | | | 8 |

Figure 5:
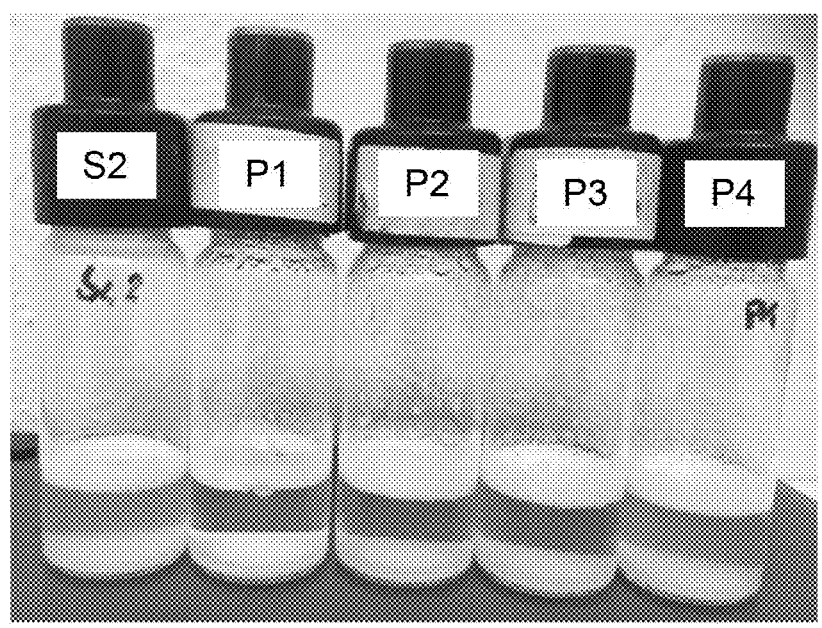
FIG. 5 depicts five vials with varying degrees of sedimentation—S2 is SCULPTRA and P1 is characterized as 150 mg of unsterilized PLLA in 8 mL water; P2 is characterized as 150 mg of unsterilized PLLA and 90 mg of CMC in 8 mL of water; P3 is characterized as 150 mg of unsterilized PLLA, 90 mg of CMC, and 127.5 mg mannitol in 8 mL of water; and P4 is characterized as 150 mg of unsterilized PLLA and 180 mg of CMC in water. See table 2 for reference.

FIG. 5 identifies the degree of foaming and sedimentation for samples S2, P1, P2, P3, and P4 from Table 3.

Figure 6:
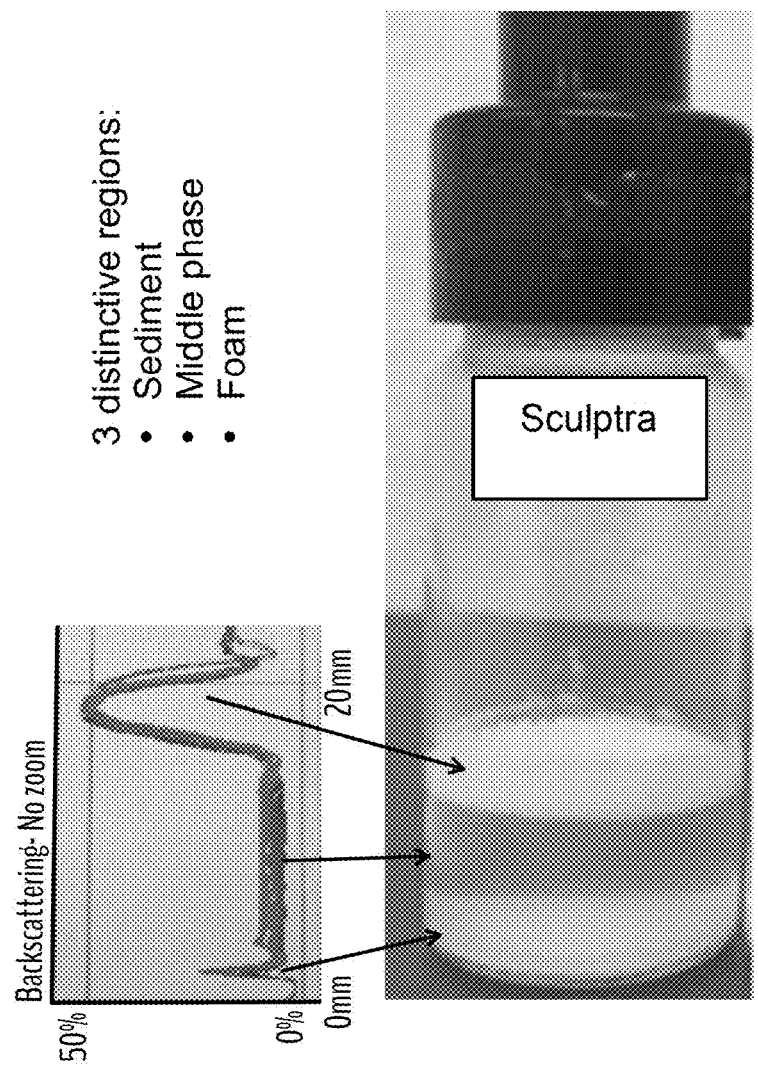
FIG. 6 depicts a turbiscan backscattering output identifying the various peaks and plateaus with the three distinct regions found in SCULPTRA/PLLA formulations—sediment, middle phase, and foam.

Turbiscan backscattering and transmission were utilized to assess the various phases of the samples—sediment phase, middle phase, and foam phase (FIG. 6).

Figure 7:
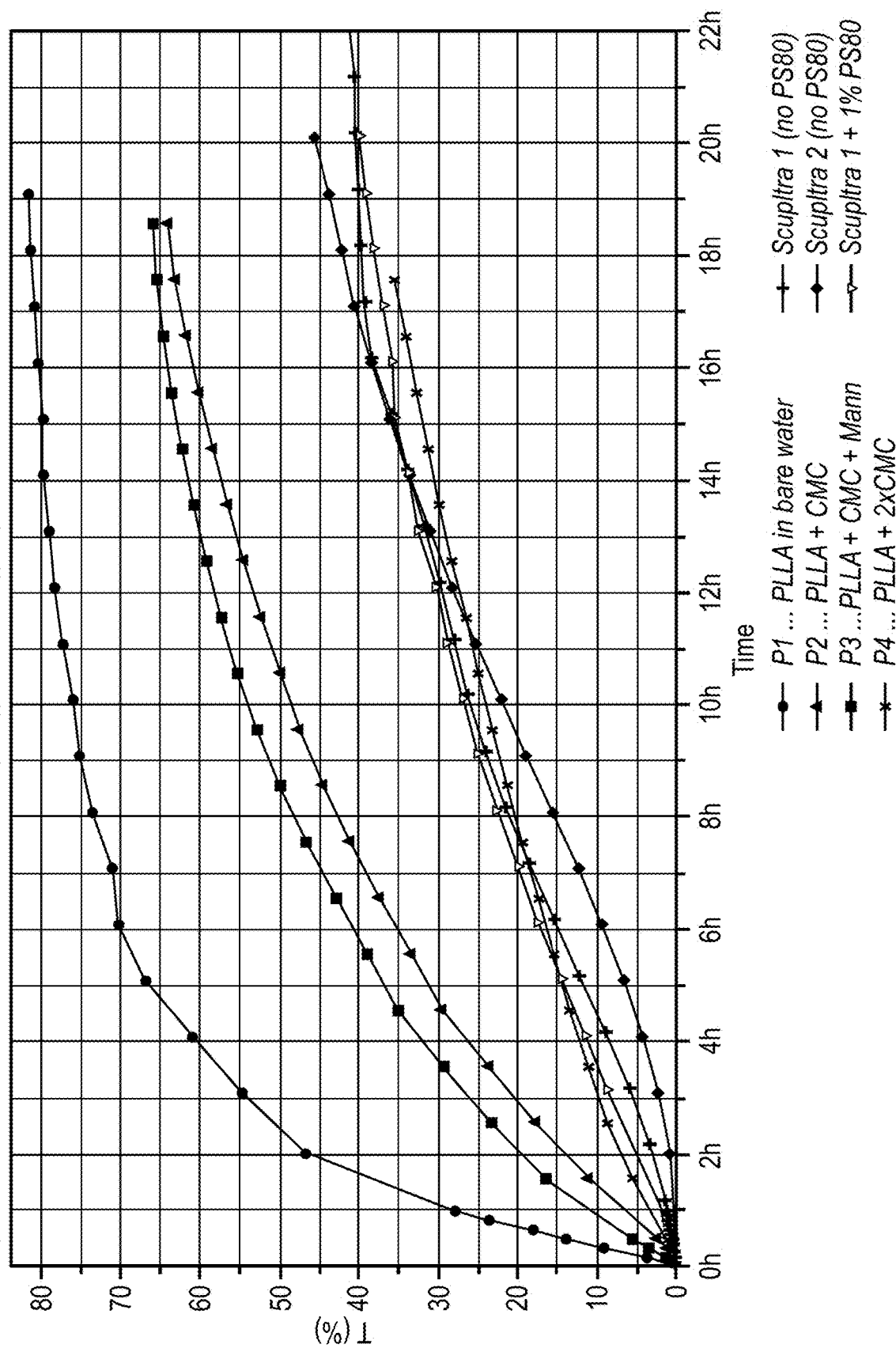
FIG. 7 depicts the transmission values for seven SCULPTRA/PLLA formulations and evaluating the effects of viscosity modifiers and PS80.

The effects of viscosity modifiers and PS80 are apparent in the transmission results for the middle phase (FIG. 7). The samples exhibit a slower sedimentation if viscosity modifiers are added, CMC exhibits a significant effect, and the effects of mannitol are negligible. PS80 has a small effect on sedimentation rate. The backscattering results are less pronounced as the transmission results.

Figure 8:
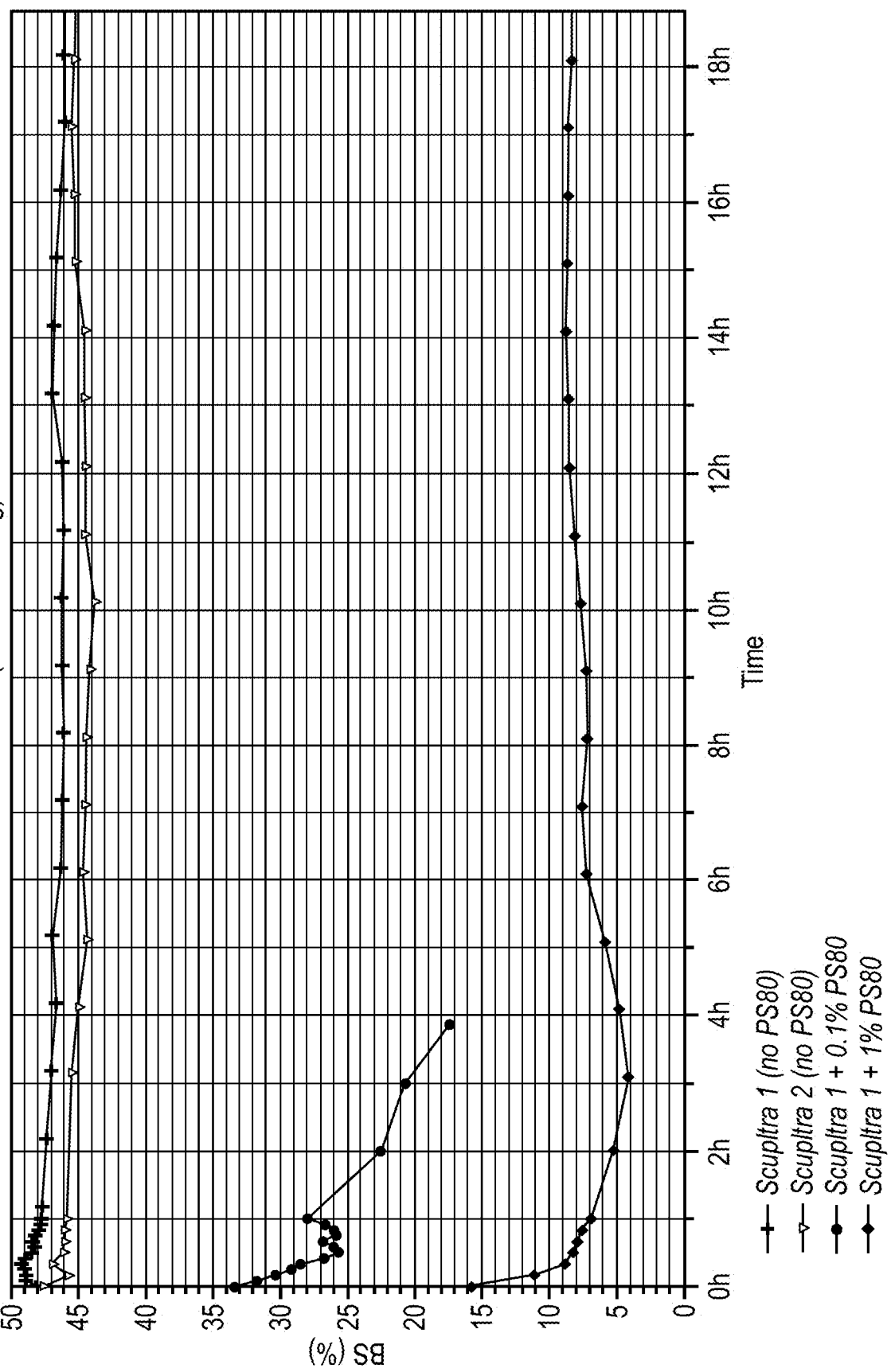
FIG. 8 depicts the backscattering values for the foam of four SCULPTRA/PLLA formulations.

The addition of PS80 to SCULPTRA samples results in a significant decrease in foaming (FIG. 8). The PS80 studies indicate that the addition of between 0.1% and 1% leads to quick disappearance of foam, after shaking, to a sample exhibiting PLLA foaming.

TABLE 4

Eight SCULPTRA/PLLA Samples

| Label | Description | PLLA (mg) | CMC (mg) | Buffer (mL) | PS80 | 10% PS80 |
|---|---|---|---|---|---|---|
| P3 | PLLA/CMC/Mannitol (1 month) | 150 | 90 | 8 | | |
| P4 | PLLA/2xCMC (1 month) | 150 | 180 | 8 | | |
| PA-1 | PLLA/buffer | 150 | | 8 | | |
| PA-2 | PLLA/buffer/PS80 | 150 | | 7.6 | 0.5% | 400 µL |

TABLE 4-continued

Eight SCULPTRA/PLLA Samples

| Label | Description | PLLA (mg) | CMC (mg) | Buffer (mL) | PS80 | 10% PS80 |
|---|---|---|---|---|---|---|
| PA-3 | PLLA/buffer/CMC | 150 | 90 | 8 | | |
| PA-4 | PLLA/buffer/CMC/PS80 | 150 | 90 | 7.6 | 0.5% | 400 µL |
| PA-5 | PLLA/buffer/2xCMC | 150 | 180 | 8 | | |
| PA-6 | PLLA/buffer/2xCMC/PS80 | 150 | 180 | 7.6 | 0.5% | 400 µL |

The PA-1 to PA-6 samples of Table 4 are in 10 mM PBS, pH 6.2, and 3 mg/mL lidocaine.

Figure 9:
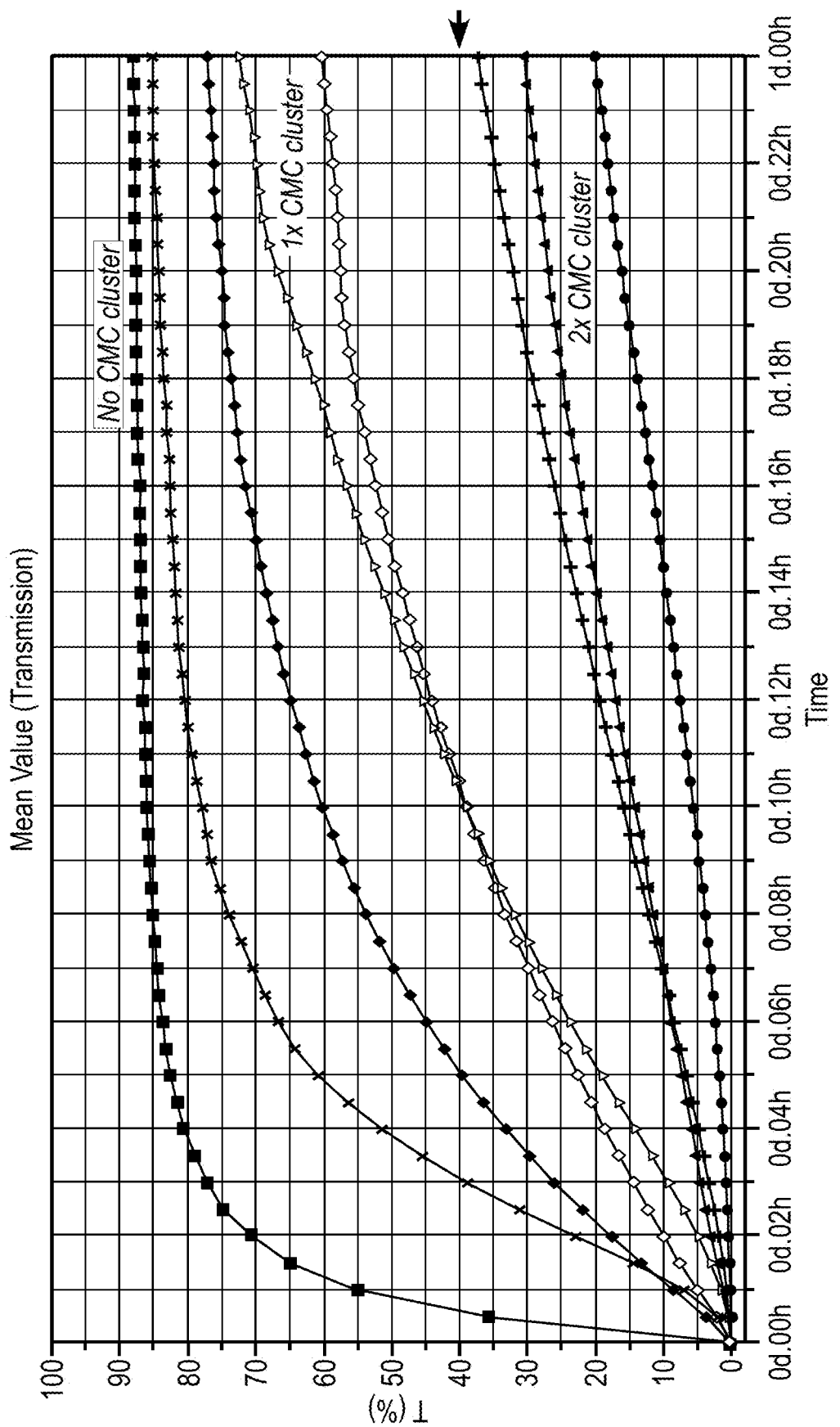
FIG. 9 depicts the transmission values for eight SCULPTRA/PLLA formulations, particularly for the middle phase for each of the formulations. The arrow in the right side of the figure indicates the value for SCULPTRA after 22 hours is ~40% transmission.

FIG. 9 depicts the transmission values for eight SCULPTRA/PLLA formulations, particularly for the middle phase for each of the formulations. The arrow in the right side of the figure indicates the value for SCULPTRA after 22 hours is ~40% transmission. There was no major difference due to storage time of CMC containing samples. There were no major differences in buffered samples. There was a decrease in the transmission in the presence of PS80, likely due to the decrease in the particles in the foam entering the middle phase, thus increasing turbidity.

Figure 10:
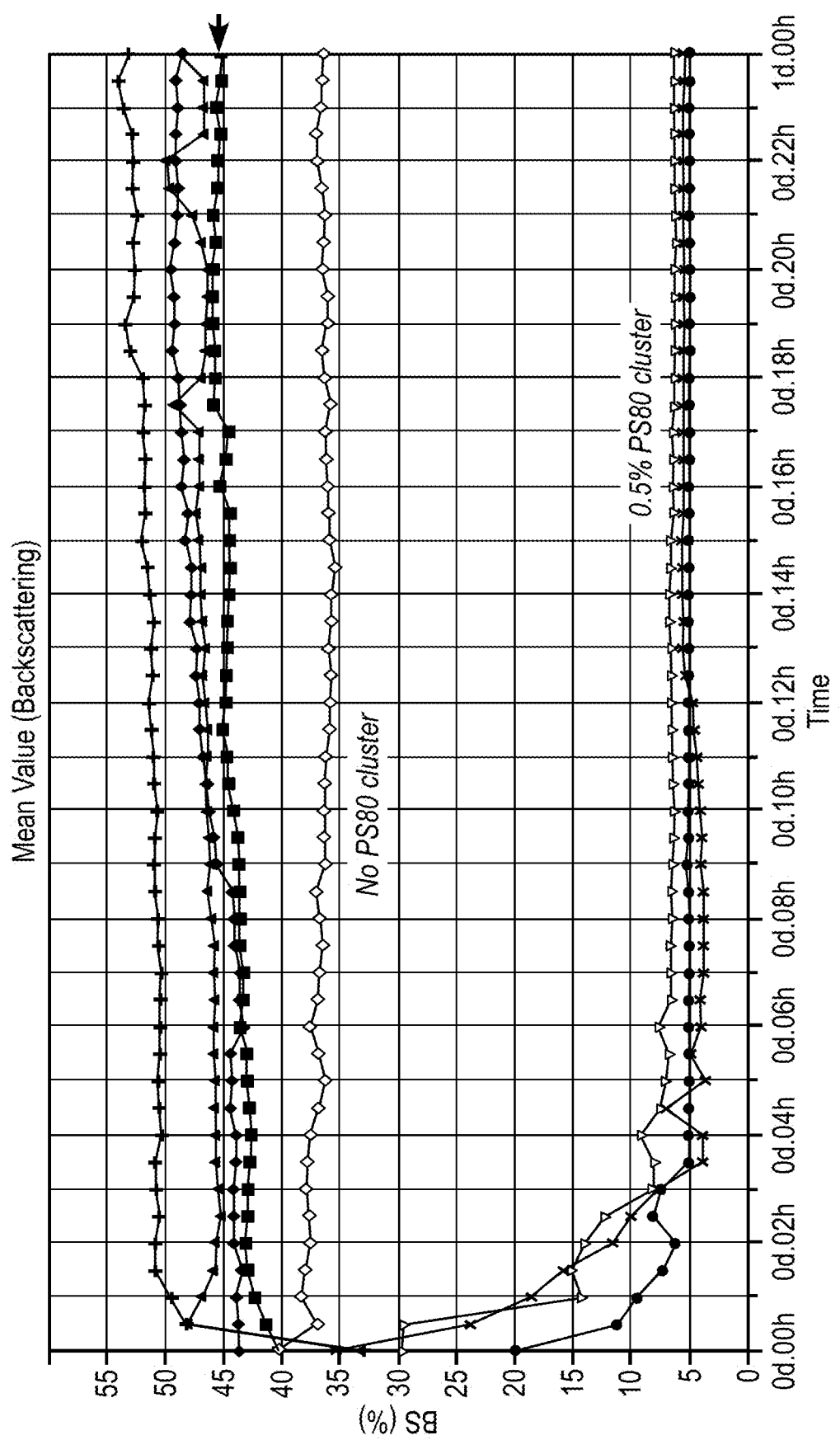
FIG. 10 depicts the backscattering values for eight SCULPTRA/PLLA formulations, particularly for the foam phase for each of the formulations. The arrow in the right side of the figure indicates the value for SCULPTRA after 22 hours is ~45% backscattering—drastic differences with the presence of PS80.

FIG. 10 depicts the backscattering values for eight SCULPTRA/PLLA formulations, particularly for the foam phase for each of the formulations. The arrow in the right side of the figure indicates the value for SCULPTRA after 22 hours is ~45% backscattering—drastic differences with the presence of PS80. In the presence of PS80, rapid breaking of the foam occurs.

The CMC aids in avoiding the sedimentation of PLLA particles due at least in part to its viscosity, but CMC has no relationship with PLLA foaming. The addition of PS80 acts by both avoiding the PLLA foaming and by also slowing down the sedimentation of PLLA particles, as compared to a mixture of only PLLA and CMC.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the disclosure claimed. Thus, it should be understood that although the present disclosure has been specifically disclosed by preferred embodiments and optional features, modification and variation of the disclosure embodied therein herein disclosed may be resorted to by those skilled in the art, and that such modifications and variations are considered to be within the scope of this disclosure.

The disclosure has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein. The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

One skilled in the art readily appreciates that the present disclosure is well adapted to carry out the objects and obtain the ends and advantages mentioned, as well as those inherent therein. Modifications therein and other uses will occur to those skilled in the art. These modifications are encompassed within the spirit of the disclosure and are defined by the scope of the claims, which set forth non-limiting embodiments of the disclosure.

In addition, where features or aspects of the disclosure are described in terms of Markush groups, those skilled in the art will recognize that the disclosure is also thereby described in terms of any individual member or subgroup of members of the Markush group.

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

What is claimed:

1. A ready-to-use composition comprising:
   (a) microspheres or microparticles of at least one polymer of non-animal origin selected from the group consisting of lactic acid polymers, glycolic acid polymers, and lactic acid-glycolic acid co-polymers wherein the at least one polymer occurs in an amount between 5 mg/mL and 50 mg/mL relative to the volume of the composition;
   (b) a hydrogel comprising water and a cellulose-derivative gelling agent selected from the group consisting of carboxymethylcellulose and hydroxypropylmethylcellulose, and present in an amount between 0.5% to 4% by weight, relative to the weight of the composition; and
   (c) polysorbate 80 in an amount between about 0.5% to about 1% by weight, relative to the weight of the composition; and
   wherein the composition exhibits a decreased rate of sedimentation by at least 5% relative to a control composition lacking the cellulose-derivative gelling agent in an amount between 0.5% to 4% by weight, relative to the weight of the composition; and wherein the composition exhibits a decreased amount of foaming due to aggregation of the microparticles or microspheres by at least 5% relative to a control composition lacking the polysorbate 80 in an amount between about 0.5% to about 1% by weight, relative to the weight of the composition.

2. The composition of claim 1, wherein the at least one polymer is a lactic acid selected from the group consisting of poly-L-lactic acid, poly-D-lactic acid, and mixtures thereof.

3. The composition of claim 2, wherein the at least one polymer is poly-L-lactic acid.

4. The composition of claim 1, wherein the cellulose-derivative gelling agent is carboxymethylcellulose.

5. The composition of claim 1, wherein the cellulose-derivative gelling agent occurs in an amount of 2% by weight, relative to the weight of the composition.

6. The composition of claim 1, wherein the polysorbate 80 occurs in an amount of about 0.5% by weight, relative to the weight of the composition.

7. The composition of claim 1, wherein the composition exhibits a viscosity between 5 to 45 mPas.

8. The composition of claim 1, wherein the ratio between the cellulose-derivative gelling agent and the polysorbate 80 is between about 10:1 to about 1:1.

9. The composition of claim 1, wherein the composition comprises the microspheres or microparticles at a concentration between 5 to 20 mg/mL, relative to the volume of the composition.

10. The composition of claim 1, wherein the microspheres or microparticles are between about 20 to 100 μm in size.

11. The composition of claim 1, wherein the microspheres or microparticles exhibit a molecular weight of between 50 to 500 kDa.

12. The composition of claim 1, wherein the composition further comprises a local anesthetic.

13. The composition of claim 12, wherein the local anesthetic is selected from the group consisting of: bupivacaine, butanilicaine, carticaine, dibucaine, clibucaine, ethyl parapiperidinoacetylaminobenzoate, etidocaine, lidocaine, mepivacaine, oxethazaine, prilocaine, ropivacaine, tolycaine, trimecaine, vadocaine, articaine, levobupivacaine, amylocaine, cocaine, propanocaine, clormecaine, cyclomethycaine, proxymetacaine, tetracaine, benzocaine, butacaine, butoxycaine, butyl aminobenzoate, chloroprocaine, larocaine, oxybuprocaine, piperocaine, parethoxycaine, novocaine, propoxycaine, tricaine; and a combination thereof.

14. The composition of claim 1, wherein the composition is aseptic.

15. The composition of claim 14, wherein the asepsis is achieved by irradiation or heat sterilization.

16. The composition of claim 1, wherein the composition further comprises sodium chloride, a phosphate buffer, and a pharmaceutically acceptable carrier.

17. The composition of claim 16, wherein the sodium chloride occurs at a concentration of 0.9% w/v, relative to the volume of the composition.

18. The composition of claim 1, wherein the composition is injectable.

19. The composition of claim 18, wherein the injectable composition is an injectable implant.

20. A pre-filled syringe or vial comprising the ready-to-use composition of claim 18.

21. An injectable implant comprising the ready-to-use composition of claim 1.

22. The injectable implant of claim 21, wherein the injectable implant is for intradermal or subcutaneous injection into a body of a subject in need thereof.

23. A method of performing reparative or esthetic dermatologic treatment, the method comprising injecting a subject with the ready-to-use composition of claim 18.

24. The method of claim 23, wherein the injection is intradermal, subdermal, subcutaneous, intramuscular, submuscular, or intragingival.

25. The method of claim 23, wherein the injection is for dermal filling, body contouring, facial contouring, or gingival filling.

26. The method of claim 25, wherein the dermal filling is selected from the group consisting of filling wrinkles, filling fine lines, filling skin cracks, filling scars, and combinations thereof.

27. The method of claim 25, wherein the facial and body contouring is selected from the group consisting of: creating pronouncements of structural features; correcting concave deformities, correcting age-related facial folds; and augmenting or repairing hard or soft tissue contour defects of the face and body due to aging, injury, and acquired or congenital deformities of the face or body.

* * * * *